United States Patent [19]

Cosentino et al.

[11] 4,136,708
[45] Jan. 30, 1979

[54] HEMODIALYSATE BLENDING SYSTEM

[75] Inventors: Louis C. Cosentino, Wayzata, Minn.; Stuart L. Gallant, Pikesville, Md.

[73] Assignee: Renal Systems, Inc., Minneapolis, Minn.

[21] Appl. No.: 804,505

[22] Filed: Jun. 8, 1977

[51] Int. Cl.$^2$ ............................................... B67D 5/52
[52] U.S. Cl. ........................................ 137/99; 222/47; 222/64; 222/137; 222/145; 417/503
[58] Field of Search ............... 222/47, 49, 64, 137, 222/145; 417/503, 534; 366/177; 137/93, 99

[56] References Cited

U.S. PATENT DOCUMENTS

| | | | |
|---|---|---|---|
| 3,499,387 | 3/1970 | Zippel | 417/399 |
| 3,605,783 | 9/1971 | Pecker et al. | 137/93 |
| 3,672,389 | 6/1972 | McConnell | 137/99 |
| 3,690,340 | 9/1972 | Sipin | 137/93 |
| 4,031,912 | 6/1977 | Lu et al. | 137/93 |

Primary Examiner—Stanley H. Tollberg
Assistant Examiner—Fred A. Silverberg
Attorney, Agent, or Firm—Schroeder, Siegfried, Ryan, Vidas & Steffey

[57] ABSTRACT

A system for preparation of variable hemodialysate in which a controllable pump meters multiple fluid sources of dialysate concentrates and water in controlled proportion. The system includes a plurality of cylinder and piston pump assemblies linked together for simultaneous operation. Individual valves connect the separate pump assemblies to the individual fluid sources to be proportioned. A position sensor provides signals indicative of the position of the pistons throughout their stroke cycle, and with a control operates the control valves associated with the individual pump assemblies in accord with functions of piston position and preselected proportioning control inputs, so as to control the volume of fluid metered by each of the pumps during the pump stroke.

24 Claims, 10 Drawing Figures

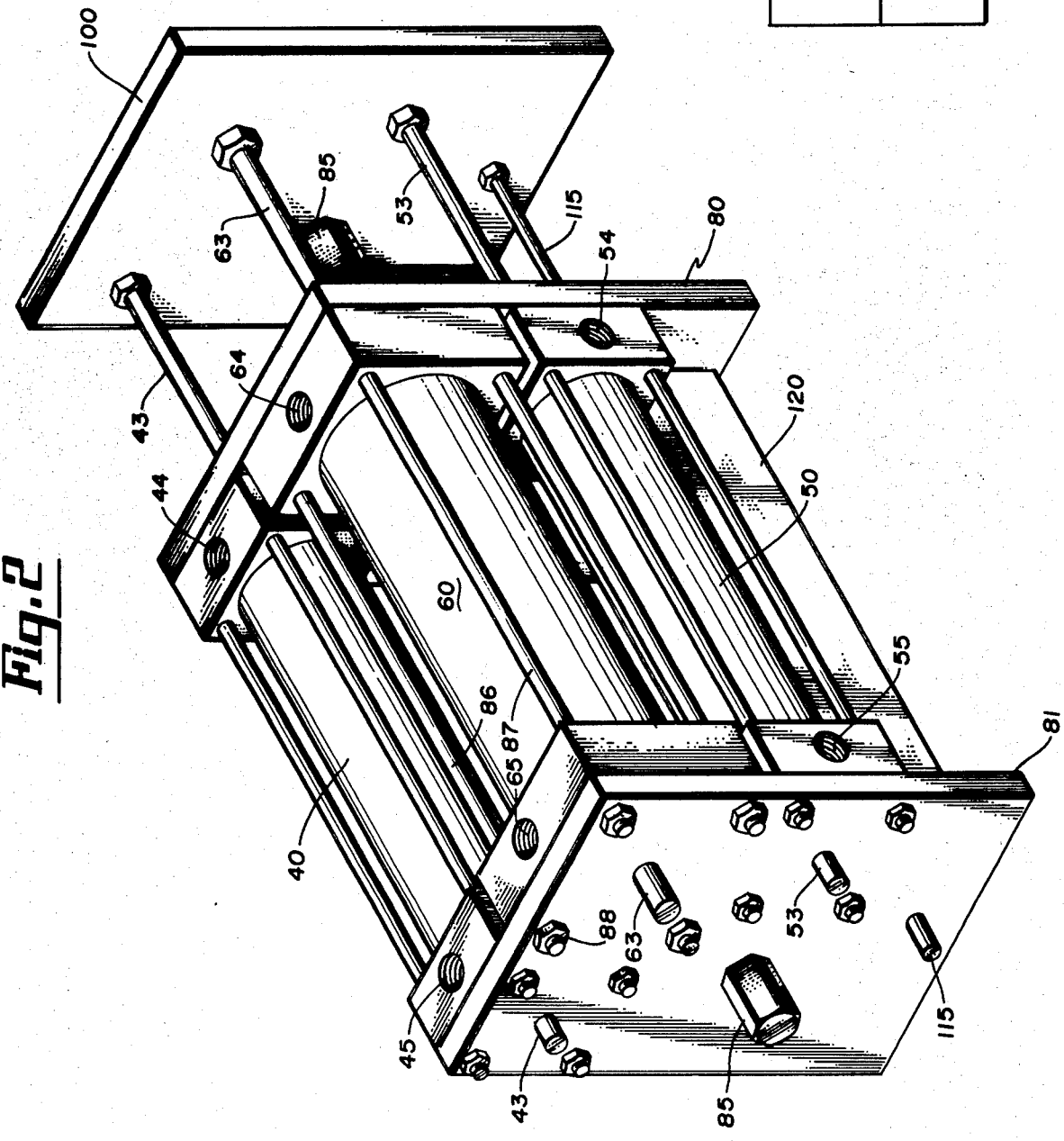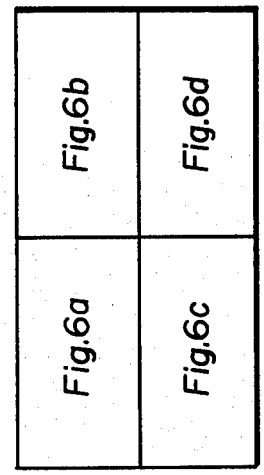

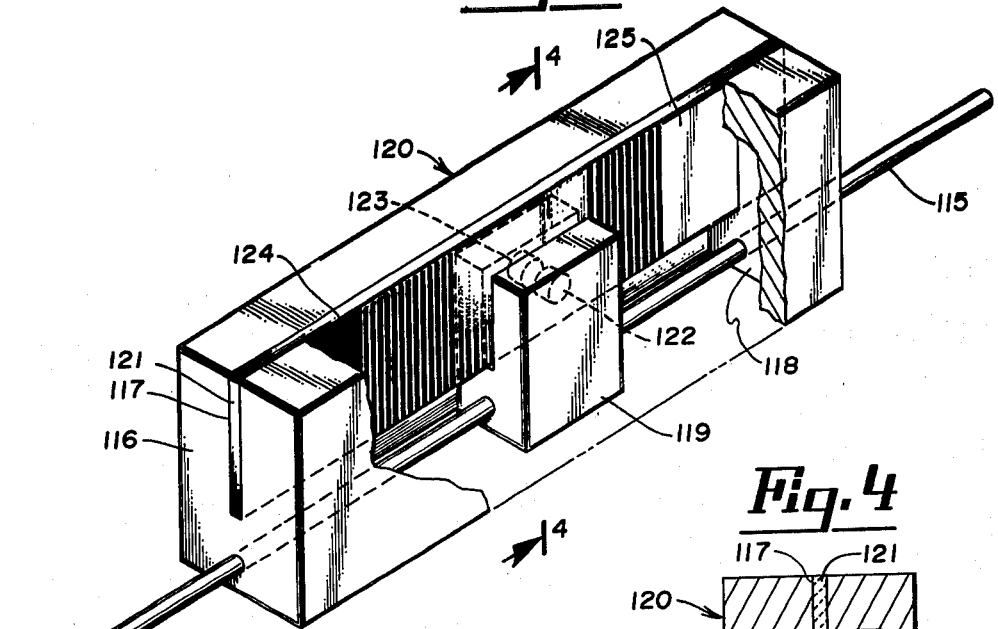
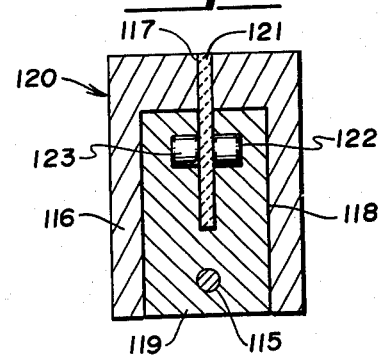

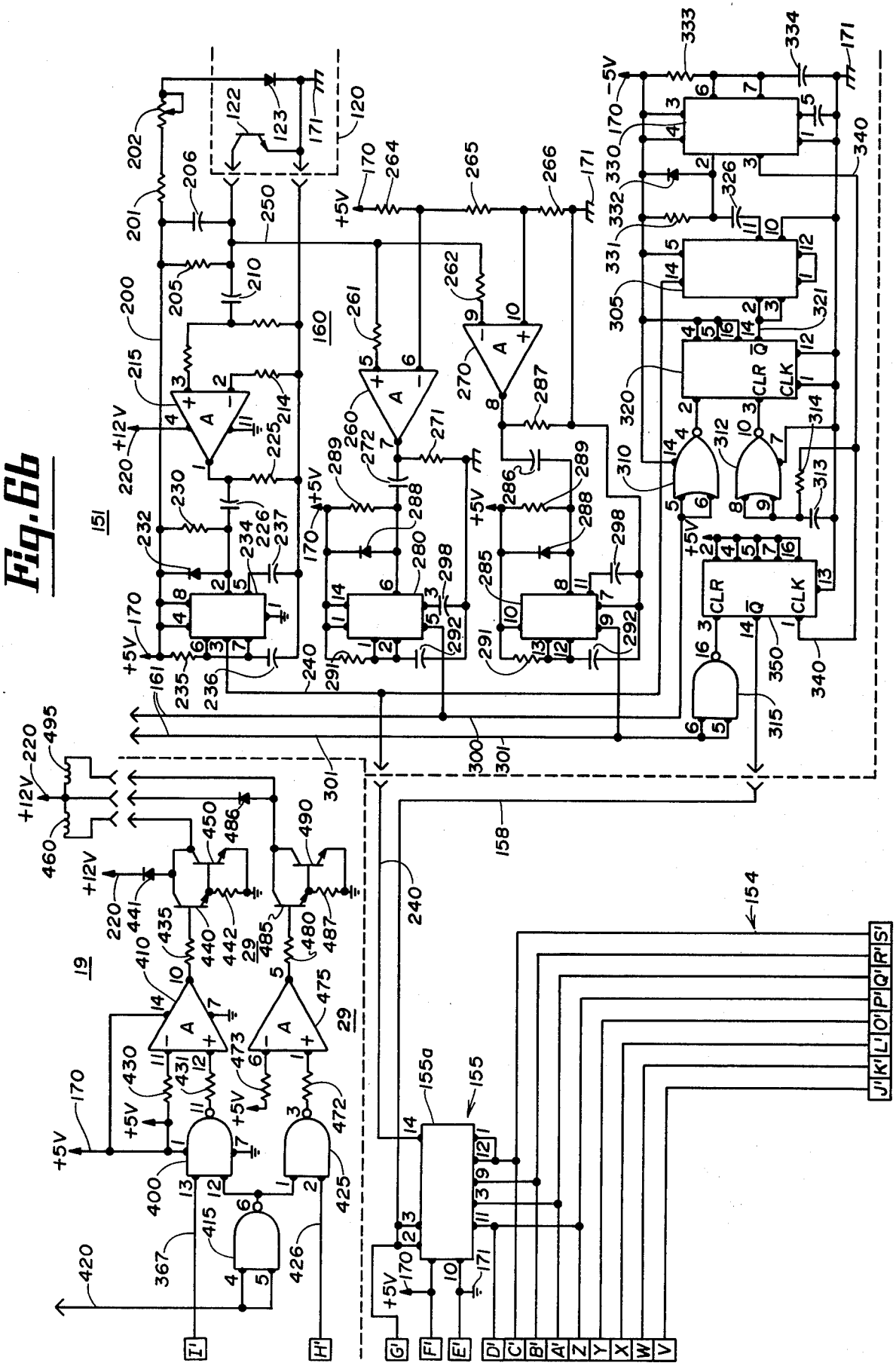

HEMODIALYSATE BLENDING SYSTEM

This invention is directed to a blending system for hemodialysate which includes controllable fluid proportioning pumps for metering and blending of multiple fluid concentrates and water in controlled proportions to one another.

BACKGROUND OF INVENTION

In many fields of industry, science, and medicine, there is need for devices or systems capable of accurately metering and then blending individual concentrates of fluid to produce a desired mixture of same. Prior art procedures perform in a generally satisfactory manner when the proportionality between the several fluids to be metered and blended is constant. These prior art techniques are not satisfactory when the proportionality between the metered quantities is variable. The prior art methods are inadequate when three or more fluid quantities must be metered according to variable precise proportions.

Although the invention set forth herein may find application in other fields, the preferred embodiment herein described will be with respect to multiple fluid concentrate proportioning for preparation of dialysate for hemodialysis.

In preparation of dialysate for use in hemodialysis, a concentrate solution is diluted with the required amount of water. The concentrate is a solution containing predetermined amounts of various ions such as sodium, potassium, magnesium, calcium, acetate, and of dextrose. Patients' needs vary as to dialysis so that the dialysate must be tailored to the patient to contain the desired concentration of ionic materials. In order to provide such tailoring, varying quantities of two or more 'standard' solutions containing the ions desired must be precisely blended. The present invention provides an accurate and convenient way for mixing controlled amounts of each of two or more concentrates with the required total amount of water to provide any desired amount of individual and collective ions in the resultant mixture.

As an illustration of the principles of the invention, consider a mix to contain both sodium and potassium ion in some predetermined and variably determinable ratio. One may start with two dialysate concentrates having in each the predetermined concentration of sodium ions. One concentrate will also include potassium ions. It is thus possible (within limits) to independently control the amounts and, therefore, the ratio of potassium and sodium ions in the final mixed dialysate. Control of this type is accurately and conveniently provided by the present invention by merely dialing in the desired concentrations of potassium and sodium ions on input switches. The system then automatically meters an amount of water and amounts of the two concentrate solutions in the proper proportion to give the desired dialysate makeup.

SUMMARY OF THE INVENTION

According to the present invention, there is provided apparatus for metering multiple fluid concentrate sources in controlled proportion, including a plurality of pump assemblies, including one such assembly for each of the fluid concentrate sources. The pump assemblies are linked together for simultaneous operation. The pump assemblies are respectively in fluid connection with individual concentrate sources. The fluid connection includes valves associated with individual pump assemblies for controlling fluid flow to and from the pump assemblies. Position sensing means associated with the pump assemblies produce signals indicative of the position of the piston of the pump assemblies in their stroke cycle. Control means are provided which respond to the position indicating signals to individually control the operation of the valve associated with the individual pump assemblies in accordance with predetermined piston position. Thus, there is control of the volume of fluid delivered by each of the pump assemblies during a pump stroke. Input selection means may be provided for selecting the desired proportions, and the control means in turn selects the functions of piston position to achieve the selected proportions. Thus, the improved controllable fluid proportioning pump system of the invention provides an arrangement for metering precise amounts of different fluids through predetermined displacement of various pump assemblies and operation of valves associated therewith. It further provides an arrangement for mixing the fluids in one of the pump chambers and introducing the fluid being metered and pumped into both sides of the pump assemblies to insure prime of the pumps. The improved pump assembly is operated from a single motive source and is tied together for simultaneous and similar movement with an encoder means for determining the pump position.

BRIEF DESCRIPTION OF THE DRAWINGS

In the drawings,

FIG. 2 is a perspective view of a pump assembly and encoder assembly which may be used in the system of FIG. 1;

FIG. 3 is an enlarged perspective view of the position sensor encoder portion of the pump assembly of FIG. 2 with parts broken away;

FIG. 4 is a sectional view of the encoder assembly of FIG. 3 taken along the lines 4—4 therein;

DESCRIPTION OF THE PREFERRED EMBODIMENT

Figure 1:
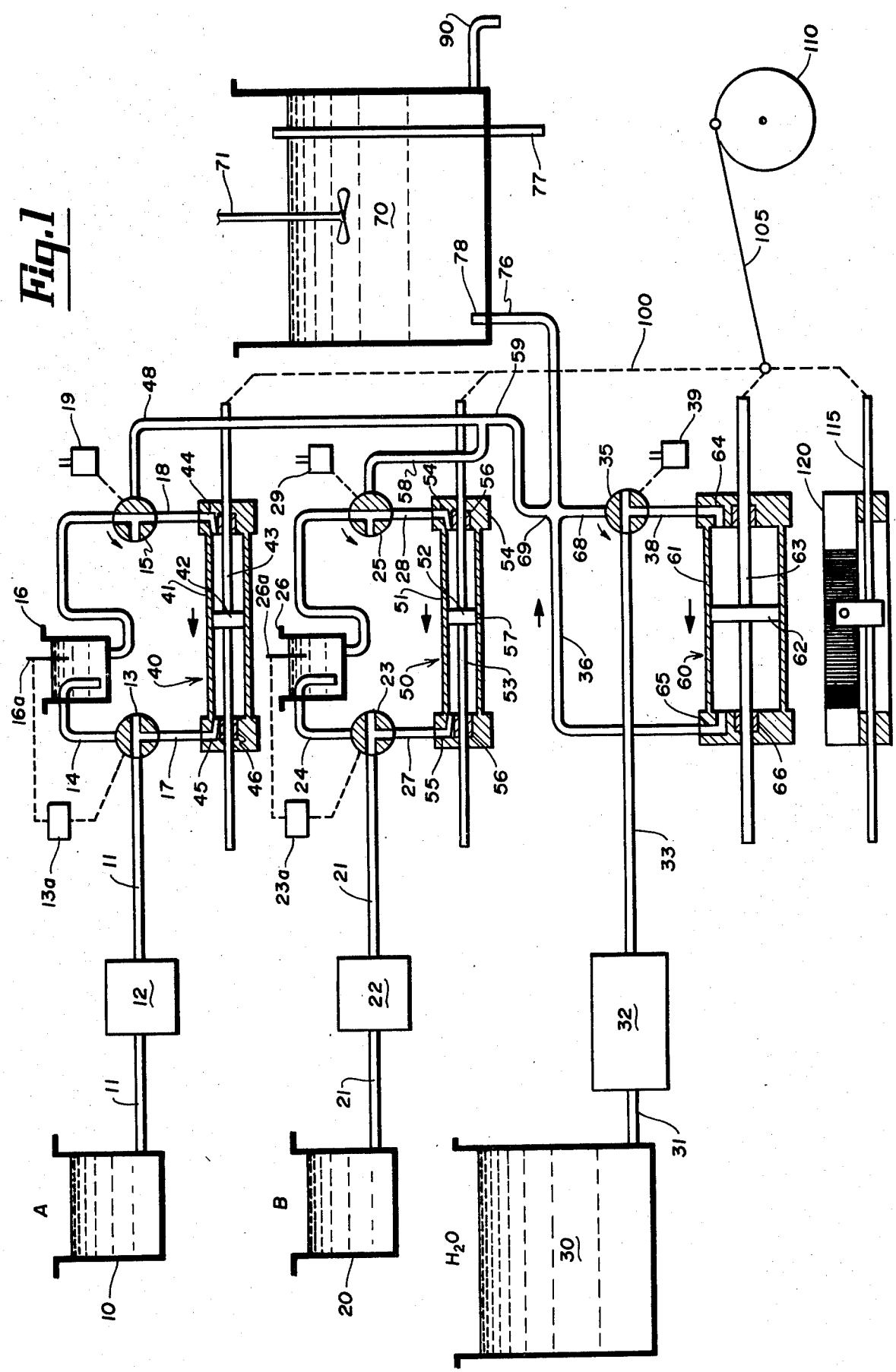
FIG. 1 is a schematic diagram of a controllable multiple concentrate source proportioning system according to the present invention as applied to mixing of a dialysate solution for use in hemodialysis.
Figure 5:
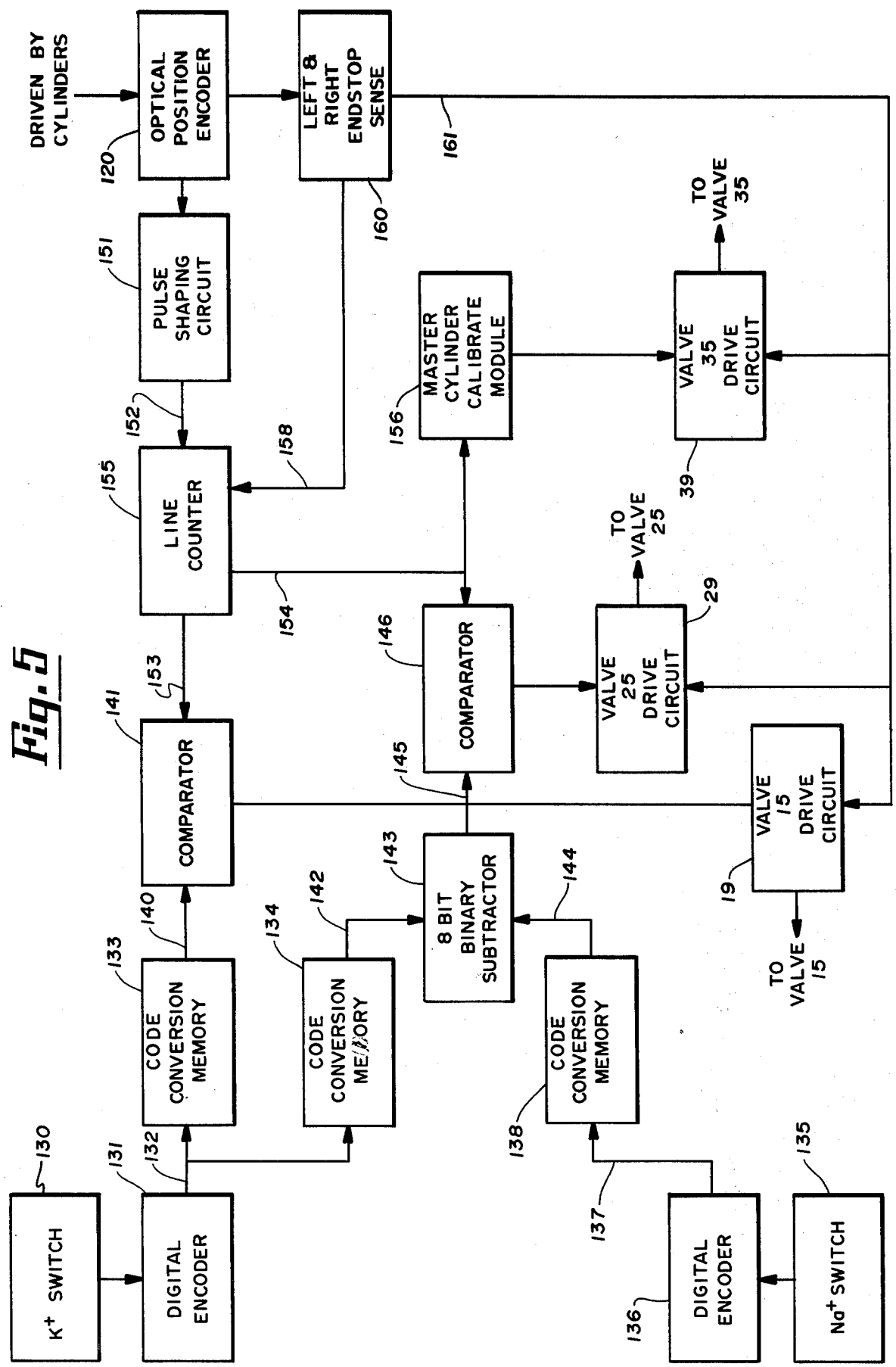
FIG. 5 is a block diagram of a control means for the multiple fluid proportioning system of FIG. 1; and, FIG. 6, formed of FIGS. 6a, 6b, 6c, and 6d, is a schematic circuit diagram of the control means for the multiple fluid proportioning system of FIG. 1 as shown in the block diagram of FIG. 5.
Figure 6A:
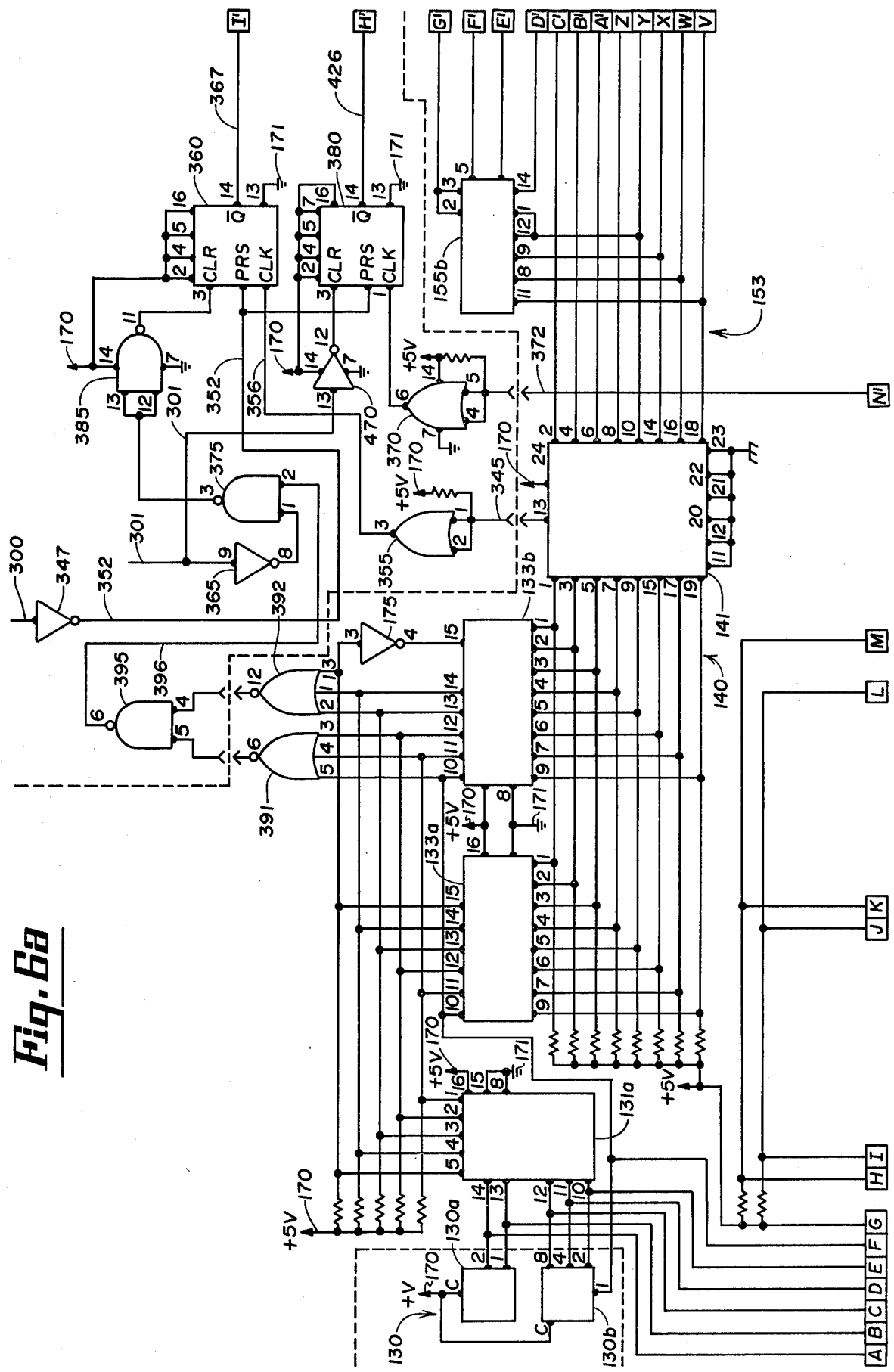
Figure 6C:
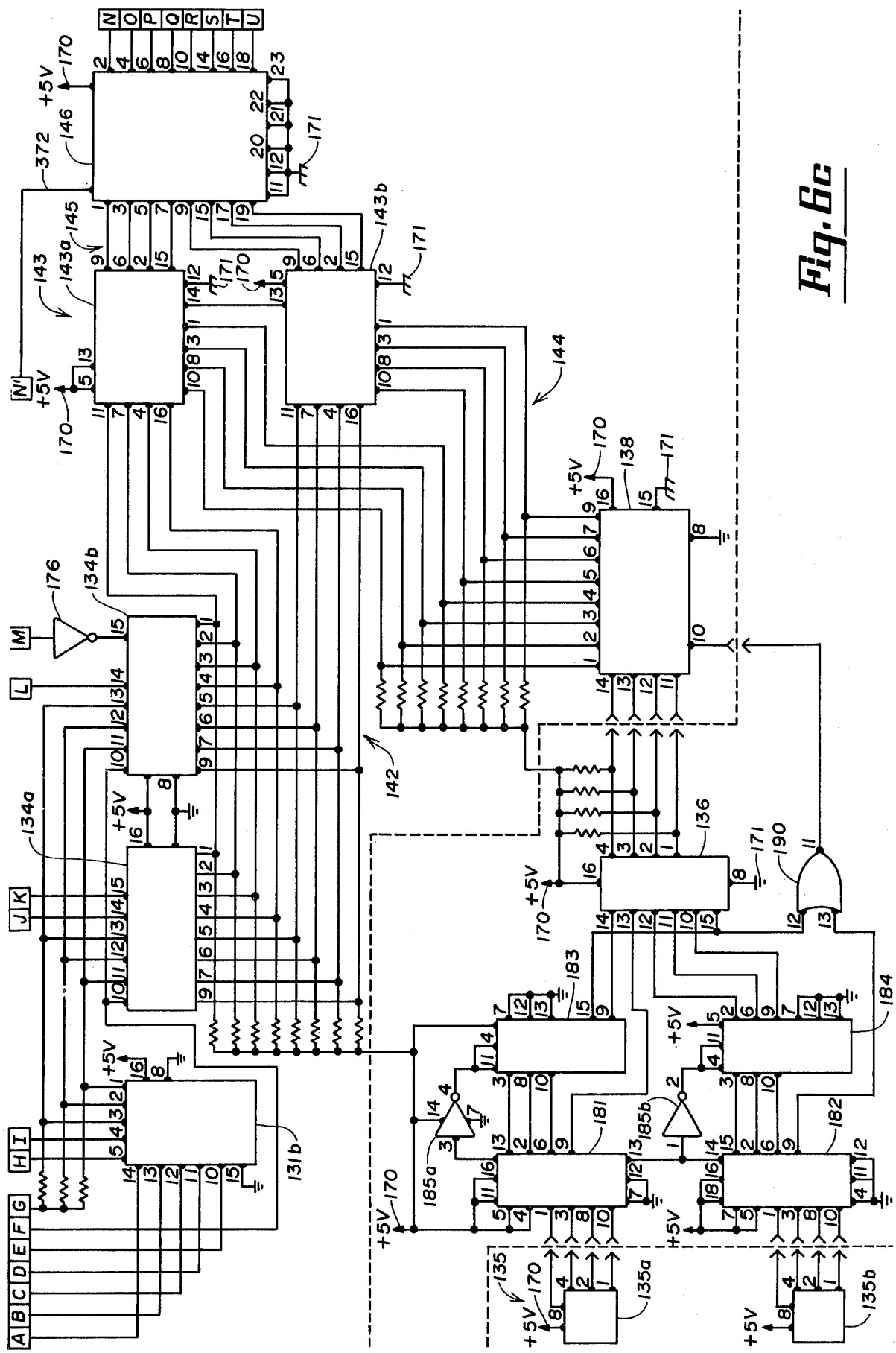
Figure 6D:
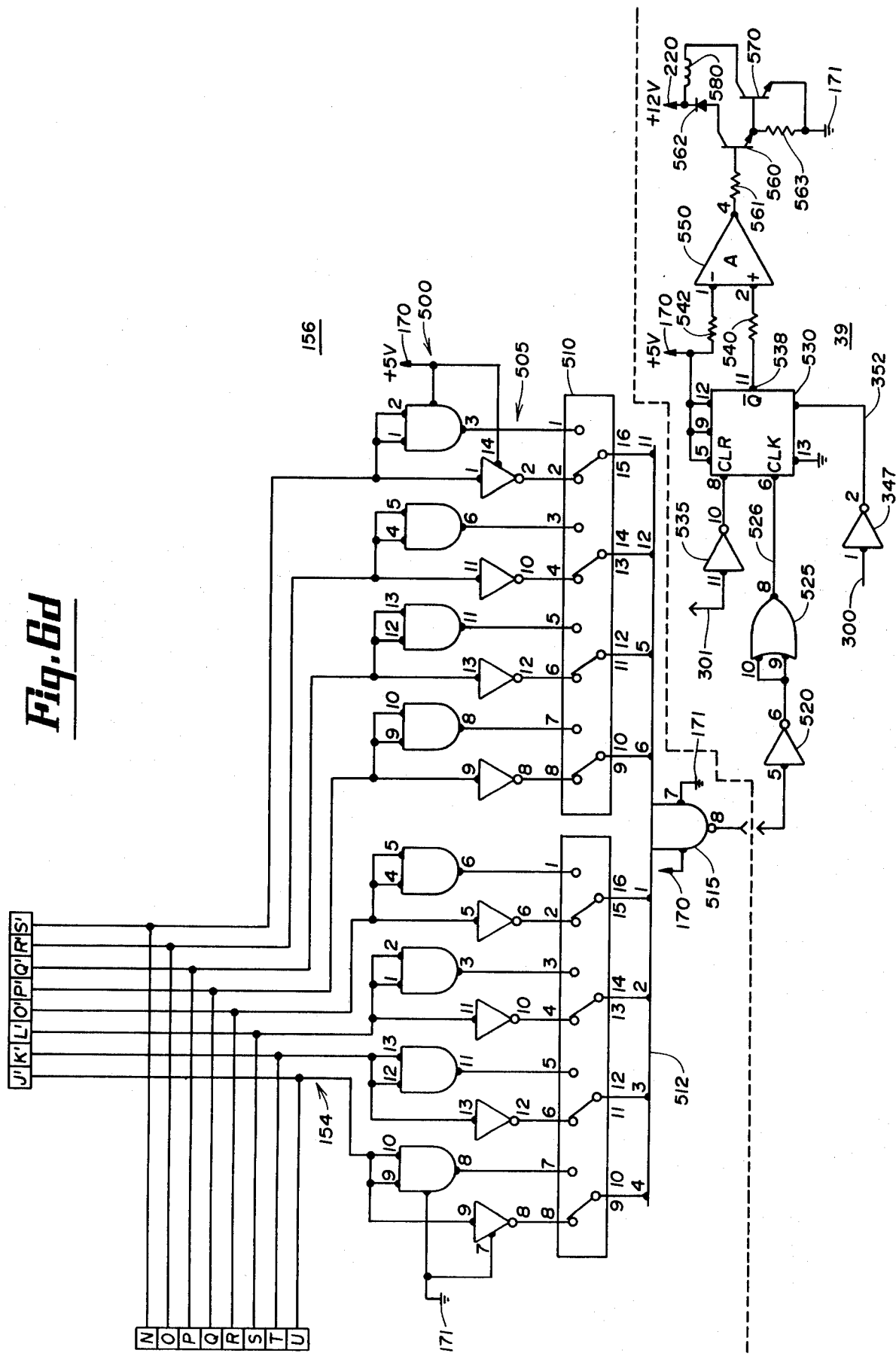

The drawings disclose our improved controllable fluid proportioning pump in connection with apparatus for mixing dialysate concentrates with water in the preparation of a dialysate solution used in hemodialysis. FIGS. 1, 5, and 6 in particular illustrate a system and control for proportioning two dialysate concentrates with water in the precise control and mixing of the desired final dialysate solution. FIGS. 2, 3, and 4 cover details of the fluid proportioning pump and control therefor.

Thus, in FIG. 1, reference numbers 10 and 20 generally designate respectively sources of the first dialysate concentrate, labeled "A" in the drawing; a second dialysate concentrate, labeled "B" in the drawing. Reference numeral 30 designates a source of water to be mixed therewith for dilution. The function of the system in FIG. 1 is to deliver water, concentrate "A" and concentrate "B" in accurately controlled and adjustable proportions for blending together in preparation of a final dialysate solution. Thus, the sources 10, 20, and 30 are connected to metering and pumping assemblies evidenced by pumps 40, 50, and 60 in which selected and correct proportions of the respective solutions are metered, mixed, and fed to a holding chamber, indicated at 70.

The solution is continually mixed while in the holding chamber, which also acts as a storage tank. When needed, the dialysate is delivered to a point of usage by conduit 90.

Referring to FIG. 1, the source vessel 10 is connected by a pipe 11 having an ionic conductivity meter 12 therein to a three-way valve 13. One port of valve 13 connects to a head vessel 16 by pipe 14. The outlet of vessel 16 is connected to a valve 15 which controls input of the concentrate A to one side of the pump 40. Similarly, the source 20 is connected by a pipe 21 (having an ionic conductivity meter 22 therein) via a valve 23 to pipe 24 and head vessel 26. The outlet of head vessel is connected to valve 25 which controls input of concentrate B to one side of the pump 50. The water source 30 is connected by a pipe 31 through a water heater 32 and a pipe 33 to one side of a control valve 35 controlling input of water to one side of the pump 60. The ionic conductivity meters 12 and 22, although not required, may be used as a safety measure to check the solutions coming from sources A and B to be sure that they have not been interchanged by a careless operator. They form no part of the control for metering and mixing. Similarly, the heater 32 conditions the water when the invention is to be used for preparation of a dialysis solution.

The valves 15, 25, and 35 as shown in the drawing are conventional three-way valves with a first side of each connected to the respective pumps with which they are associated. Each have a separate actuator 19, 29, and 39 respectively which switch the valves between operative positions. Although shown rotary, it will be understood that the valves may be of a known type using linear movement with port arrangements to affect a three-way valving action. The pumps 40, 50, and 60 are piston pumps each employing a cylinder 41, 51, and 61 and reciprocating each piston 42, 52, and 62 with ports at each end of the pumps. Thus, as shown schematically in FIG. 1 and pictorially in FIG. 2, the pump 40 includes a cylinder 41 with a closure at opposite ends including ports 44 and 45 at the ends of the same. A reciprocating piston 42 within the cylinder is mounted on a shaft 43 which extends through the ends of the pump for reciprocation of the piston. Suitable guide and seal members 46 are included at each end of the cylinder. Similarly, the pump 50 includes a cylinder 51 with ports 54 and 55 at the ends of the same. A piston 52 is mounted on a shaft 53 for reciprocation. The shaft 53 extends beyond the ends of the cylinder and is guided and sealed therein by members 56. Pumps 60 include a cylinder 61 with a piston 62 within the cylinder mounted on the shaft 63 which extends beyond the ends of the cylinder and is guided and sealed through the end closure by suitable guide and seal members 66.

Pump 40 has port 44 connected by conduit 18 to the first side of the three-way valve 15. A branch passage 17 connects port 45 to a first side of valve 13. Valve 13 is a three-way valve controlled by a level sensor 16a in head vessel 16 connected to a valve drive 13a. Valve 13 controls flow into port 45 from pipe 11 and from port 45 to the head vessel 16.

Similarly, pump 50 has its port 54 connected by conduit 28 to a first side of the three-way valve 25. A branch pipe 27 connects port 55 through a first side of valve 23 to the pipe 21. Valve 23 is also a three-way valve controlled by a level control sensor 26a in a head vessel 26 connected to a valve drive 23a. Valve 23 controls flow into port 55 from the pipe 21 and from port 55 to the head vessel 26.

Pump 60 has its port 64 connected through a pipe 38 to a first side of valve 35 with the opposite side of valve 35 being connected by a pipe 68 to a pipe 36 leading to the port 65 at the other end of pump 60.

Valves 15 and 25 respectively are connected through pipes 48 and 58 to a common pipe 59 and a four-way connection 69 to a conduit 36.

It will be seen in FIG. 1 that the shafts 43, 53, and 63 of the respective pumps are connected in common through a mechanical linkage, indicated generally at 100, to be driven by a linkage 105 and a motive device 110. The common connection 100 also connects to a shaft 115 of an encoder or position sensor 120 so that the shafts of the respective pumps 40, 50, and 60 and the shaft of the encoder are moved simultaneously and in the same direction and through the same path length by the motive device 110 operating through the linkage 105.

Referring now to FIG. 2, the preferred embodiment of the pump assembly includes the plurality of piston-type pumps 40, 50, and 60 mounted in a common frame. A pair of end plates 80 and 81 are provided in spaced apart relationship to accommodate the pumps. Thus, the pump 40 with its ports 44 and 45 are secured respectively to the plates 80 and 81 as are the ports 54 and 55 of pump 50 and ports 64 and 65 of pump 60. The three cylinders 41, 51, and 61 are positioned parallel to each other between the end plates and a plurality of threaded end rod members 86 and 87 extend between the plates 80 and 81 to secure the assembly in connected relation by bolt 88. The shafts 43, 53, and 63 extend beyond the plates 80 and 81 and at one end are connected to a plate member 100 which comprises a common linkage between the shafts. Although not shown, it will be understood that the linkage 105 connected to the drive wheel 110 will reciprocate the plate 100 and hence all three shafts 43, 53, and 63 to reciprocate the pistons within the respective cylinders. A suitable hexagonal rod 85 serves as a guide and is connected to plate 100 and extends through the plates 80 and 81 to guide the movement of the shafts and prevent binding the same. Similarly, the linkage 115 for the encoder or position sensor 120 is connected to the plate 100 and extends through the plates 80 and 81 to move with the plate and indicate the position of the pistons within the cylinders as will be described below. The encoder 120 is physically secured between the plates 80 and 81 and has a length equal to the length of the cylinders.

Referring to FIG. 1, it will be seen that the pump assemblies 40, 50, and 60 have fluids introduced to each side of the piston associated therewith to assure maintaining prime in the system and in each pump. It will also be appreciated that as the pistons of the pump assemblies are moved back and forth, the volume of fluids sent by each of the pump assemblies to the ultimate mixing chamber 70 are determined both by the timing of the opening and closing of the valve associated with each pump assembly as well as by the diameter of the pump chamber. Thus, as the pistons of the pump assemblies are moved from right to left or in the direction of the arrows, fluid will be introduced into the right-hand end of the cylinders through the respective ports 44, 54, and 64 filling the cylinder behind the moving piston. In the case of the pumps 40 and 50, this fluid or the concentrate is supplied from head vessels 16 and 26. The left-hand end of the cylinders will have been filled on the previous stroke in the opposite direction from the sources 10 and 20 through valves 13 and 23. Thus, fluid on the left-hand end of the cylinder 40 will be fed from the port 45 to the head vessel 16 to maintain its level, or if the vessel is at the set level, the concentrate will be directed through the valve 13 back to the source 10. The same fluid flow takes place in the pump assembly 50 wherein fluid from the left-hand side of the cylinder is directed through the port 55 to the head vessel 26 to maintain its level or it will be directed back to the source 20. In each of these pump assemblies 40 and 50 during the preceding piston stroke in the opposite direction, fluid will have been drawn in from the respective sources 10 and 20 through the conductivity meters and valves 13 and 23 into the branch passages 17 and 27 to fill the left-hand side of the cylinder as fluid on the right-hand side of the cylinder is ejected through the valves 15 and 25 to the outlet conduits 48 and 58. The amount of fluid being ejected on this direction of stroke will be dependent on how long the particular valves 15 and 25 are positioned to connect the pipes 18-48 and 28-58 respectively.

Since each of the valves are operated independently, the timing of the three-way valve to the open position to direct fluid in the respective outlet conduits 48 and 58 will be controlled by the preselected volume of concentrate to be metered from the respective pumps. As soon as the desired volume has been metered (as determined by the position of the piston within the cylinder on this direction of stroke), the valves 15 and 25 will each turn to a new position and cause the remaining fluid in the outflow side of the pump to be directed back to the head vessels 16 and 26.

Valve 35 is switched to the intake of water position to permit water to flow from conduit 33 during the movement of piston 62 as shown by the arrow in FIG. 1. The opposite side of the cylinder will have a mixture of water and dialysate condensate, as will be hereinafter described, which will be ejected on this intake of water stroke. With valve 35 switched to the opposite position, on movement of piston 62 to the right, the water in the right-hand end of the cylinder will be ejected via port 64 through the pipe 38 and valve 35 to the conduit 68 and four-way connection 69 to the pipe 36 and the opposite or left-hand manifold 65.

In this direction of movement of the pistons which is opposite to the arrows in FIG. 1, the valves 15 and 25 will be metering the dialysate solutions A and B from the sources 10 and 20 to the outlet conduits 48 and 58. This flow will be directed to the four-way connection 69 and mixed with the water being directed from the right-hand end of the cylinder of the pump 60 in the left-hand end of the cylinder. Any underflow or amount less than the capacity of this end of the cylinder will be drawn directly from the holding chamber 70 through conduit 76 into the left-hand end of pump 60. This forces the water and a portion of the dialysate concentrate from the pump assemblies 40 and 50 into the left-hand end of the cylinder 61 for premixing purposes.

Ultimately, this premixed fluid will be ejected through the conduit 36, connection 69, and pipe 76 into tank 70. As the respective pistons 42, 52, and 62 are reciprocated within the respective cylinders of pumps 40, 50, and 60, a movable element 119 of the position sensor 120 is moved within its frame in accordance with the position of the pistons.

The encoder or position sensor 120 is shown in FIGS. 3 and 4. It includes a base 116 which is generally block-like in structure having a suitable slot 117 positioned therein and a generally hollow interior 118 in which the movable element or block member 119 is positioned. The block member is carried by the shaft 115. Slot 117 mounts a grid 121 having spaced parallel lines with opaque and transparent material thereon extending substantially the length of the recess in base 116 and corresponds to the extent of piston movement. Block member 119 is generally "U" shaped in form with a slot therein to ride along the opposite edges of the grid. One side of the block member 119 mounts a photocell or phototransistor, indicated at 122, and at the other side, a corresponding light source or light-emitting diode 123. The opaque lines in the grid 121 block the light falling on the photocell while the transparent surfaces or lines therebetween provide for transmission of the light to the photocell. The ends of the grid 121 have solid opaque or transparent surfaces 124 and 125 respectively, to indicate left- and right-hand end stop sections of the same. In this manner, a line counter is provided which corresponds with the length of travel of the pistons. The output of the photocell, as the shaft 115 is moved back and forth within the frame 116, will count the plurality of lines corresponding with the length of travel of the pistons. The count will occur in either grid direction, depending upon which end of the grid the count is started, but, as will be hereinafter noted, is effective only on the pumping stroke. It will, however, determine or indicate piston position for the purpose of defining the amount of fluid ejected from a cylinder with movement of the pistons.

FIG. 5 shows a block diagram of the electronic valve control circuit for the proportioning pumps as applied to the dialysate mixing system of FIG. 1. This circuit is shown in detail in FIG. 6. The reference numeral 130 indicates an operator setable switch for allowing operation personnel to dial the desired amount of potassium into the dialysate solution. Switch 130 connects to a digital encoder, indicated in block at 131, which connects via a data trunk 132 to a pair of code conversion memories 133, 134. The nature and operation of the code conversion memory is to be explained hereinafter. It will also be appreciated that although single lines will be used in FIG. 5 to interconnect the circuit components, such single lines involve data trunks, similar to 132, in which a plurality of parallel leads will be included according to the number of digital bits being processed.

Operator setable switch 135 allows an operator to set a sodium concentration for the dialysate solution. Switch 135 connects a digital encoder 136 which is connected by means of a data trunk 137 to a code conversion memory 138. The output of the code conversion memory 133 is connected via data trunk 140 to one input of a binary comparator 141. The output of memory unit 134 connects via data trunk 142 to one input of a binary subtractor unit, indicated in block at 143. Similarly, the output of code conversion memory unit 138 connects via data trunk 144 to the other input circuit of the subtractor unit 143, and the output of the subtractor unit 143 is applied via a data trunk 145 to the input of a second binary comparator 146. The position sensor 120, which is included in the pump assemblies, as seen in FIGS. 1 and 2, provides output pulses from the photo cell 122 in accord with the solid lines passed on the grid 121 when the pump assemblies are moved. The pulses are fed to a pulse shaping circuit 151 and by a lead connection 152 to a binary line counter 155. Line counter 155 is connected by data trunks 153, 154 to binary comparators 141, 146 and to master cylinder calibrate module 156. The position sensor 120 is also able to sense left or right end stop zones by virtue of light and dark areas 124, and 125 at the ends of the grid 121. The circuit 160 provides this function in signal form which is fed through a circuit 161 to valve drive units 19, 29 and 30 associated with the valves 25, 30 and 35 and also to line counter 155 to reset the same at the end of each stroke. The valve drive unit 19 is connected to the binary comparator 141 which compares line count with the desired piston position to provide input to the valve drive circuit for driving the electrically operated valve 15 between its two operative positions. The drive unit 29 is connected to the binary comparator 146 which also compares line count with desired piston positions and connects to the valve 25 to control a flow of concentrate from source 20. Valve drive unit 39 connects to the master cylinder calibration module 156 which receives an input from the line counter 155, and it controls the operation of the valve 35 for the pump assembly 60.

By way of examples, assume that concentrate solution "B" from source 20 in FIG. 1 contains no potassium (K+) ions but has an equivalent concentration (when diluted 35:1) of 145 mEQ/l sodium Na+ ions. Similarly, assume that concentrate solution "A" in source 10 contains an equivalent K+ ion concentration of 3.9 mEQ/l, and an equivalent sodium Na+ of 125 mEQ/l (when diluted 35:1). By appropriate proportioning of the two concentrates and water, the amounts of potassium and sodium ions in the dialysate can be independently controlled over a desired range of values. Specifically, the amount of potassium ions can be controlled between zero and 3.9 mEq/l while the amount of sodium ions can be independently varied in a range of 125-145 mEq/l.

In the present system, the cylinder for the water of pump 60 is sized with respect to the cylinders for the concentrate pumps 40 and 50 to provide the desired 35:1 water dilution. The amount of potassium or sodium ion concentration in the dialysate is then controlled by proportioning the outputs of the two concentrate cylinders or pumps by means of a control circuit of FIG. 5. If valve 25 for concentrate B is open and valve 15 for concentrate A is closed, at their output ports, through the stroke cycle of their respective pump assemblies, then dialysate having zero potassium concentrate will be produced. On the other hand, if the valve 15 only is open and valve 25 is completely shut off as far as concentrate B is concerned, a dialysate solution having 3.9 mEq/l of potassium and 125 mEq/l of sodium ions will be produced. Intermediate values of potassium and sodium call for less than a full stroke of the two solutions in accord with the following equations:

Percentage of stroke for concentrate $A =$ $$\frac{C_K}{3.9} \times 100$$

(Where $C_K$ is the potassium concentration between zero and 3.9 mEq/l.)

Percentage of stroke for concentrate $B =$ $$\frac{C_{Na} - (C_K/3.9)(125)}{145} \times 100$$

(Where $C_{Na}$ is the selected sodium concentration between 125 and 145 mEq/l.)

Referring to FIG. 5, the potassium concentration entered on switch 130 is realized by means of a digital encoder 131 and code conversion memory 133. Memory 133 is a programmable read only memory whose various memory locations hold numbers of position sensor counts corresponding to different stroke cycle percentages. Encoder 131 addresses a memory location according to the concentration entered at switch 130. Thus, if one half of the total mEq/l of potassium is entered at switch 130, encoder 131 addresses a memory location in memory 133 which has previously been loaded to a binary count equal to half the number of position sensor counts corresponding to a full stroke of the pump assembly required to deliver the full amount of potassium in the concentrate solution. As the pump assembly moves through a full stroke or in the direction of pump the concentrate through the outlet valve 15 through the pipe 48, comparator 141 compares the increasing count in line counter 155 to the desired count on lead 140 from the memory 133. When the desired point is reached, comparator 141 changes state to effect switching of valve 15 for the concentrate A solution.

Memory 134 was previously loaded with a sodium concentration values corresponding to the amount of mEq/l of sodium which will be provided by concentrate A along with the amount of potassium entered on switch 130. For example, if one half of the total mEq/l solution of potassium is required, the concentrate A solution will be pumped for half a stroke required to provide the total amount and enough sodium will also be pumped to provide one/half of the 125 mEq/l to provide a 62.5 mEq/l solution. This value is stored at an appropriate memory location in the memory 134 in terms of equivalent line counts to be addressed by the encoder 131. The control circuit supplies this partial sodium concentration in terms of line counts to the subtractor unit 143.

The total desired concentration of sodium is entered in switch 135, which causes digital encoder 136 to address a memory location in memory 138 which was previously loaded by a binary representation of the desired total sodium concentration in terms of line counts. This value was applied via the data trunk 144 to the subtractor unit 143 which subtracts the partial sodium concentration provided by solution A from the total desired sodium concentration. The difference equals the partial sodium concentration required to be supplied from concentrate B again in terms of the equivalent binary number of position sensor line counts. The desired count is compared by the comparator 146 against the actual count as the cycle progresses and the valving 25 to concentrate B is switched accordingly.

The amount of water pumped by pump 60 through its associated control valve 35 is constant for each cycle to control the 35:1 ratio of dilution between water and concentrate. Thus, regardless of the setting on switches 130 and 135, setting forth the desired potassium and/or sodium concentrations in the resultant dialysate solution, each pumping stroke of the pump 60 will move the same amount of water. If the relative size of the cylinders of pumps 60, 50 and 40 are so selected that the volume of the cylinder 61 is at least 35 times as great as the volumes of cylinders 51 and 41, then a complete pumping stroke or a complete volume of water from the cylinder 61 will be required for each pumping stroke. However, if the cylinder 61 is larger or if it is desired to change the ratio to some smaller number, the master cylinder calibrate module is adjusted to switch the associated valve 35 through its valve drive 39 at less than a complete pumping stroke to obtain the desired ratio. The end stop sense circuit 160 through its conductor or cabling 161 conditions the drive circuits 19, 29 and 39 so that valve switching is effected on the power stroke or pumping stroke of each valve only. Similarly, the end stop sense circuits provides a reset signal as indicated by the cable 158, to the line counter 155 to reset the same at the start of each pumping stroke for the respective pump assemblies.

It will be understood that the system is designed to be operated continuously with fixed switch setting for switches 130, 135. The blended hemodialysate will be pumped to the holding chamber for usage. Changes made in the switch settings to set different ratios of potassium and sodium ions in the dialysate will be made after the chamber and fluid lines are purged. The system will then be reactivated to produce a new solution of hemodialysate with the different ration between sodium and potassium ions.

Referring to the schematic circuit diagram of FIG. 6, it will be noted that the potassium selector switch 130 is formed of two switches, one for each digit, having a binary coded decimal output and identified as 130a and 130b. In the present example given for the concentrate solutions these switches may be set for any desired amount of potassium in 0.1 increments between 0.0–3.9 mEq/l of potassium from solution A or 39 separate switch steps. The switches are energized from a DC source indicated at 170 and the output signals or circuits extending therefrom are connected to a binary coded decimal to binary decoder unit, indicated at 131a. This BCD to binary decoder is of the type identified as DM74184. The numeral indications around the unit 45 represent the terminals therefrom with the unit being energized from the DC source 170 and grounded at 171. The BCD switch 130a has a manual stop inserted thereon so that it may be moved between zero and 3 as its maximum setting. The output of the decoder 131 supplies address information to the code conversion memory unit 133 shown as 256 bit bipolar electrically-programmable read-only memories 133a and 133b. Each memory is capable of producing 32 8 bit outputs and such memories are used to supply the binary output for the 39 different switch settings of the switches 130a and 130b. These read-only memories are of the type manufactured by Monolithic Memories, Inc., under type No. 6330 -J. These memories are programmed by selectively fusing links in the output stages thereof to provide for 8 bit binary output for each of the 32 inputs. As will be hereinafter noted, the line counter 155 provides an 8 bit binary output for each of the lines counted by the optical position encoder 120. Read-only memories 133a and 133b are programmed to provide a binary output which will correspond with the output of the counters 155 for the various line counts representing varying piston positions. The outputs of the memories are programmed so that their binary outputs corresponding to the various switch settings from 0.0 to 3.9 in 0.1 increments will correspond with the line count or piston movement which will provide this much potassium in the concentrate. Thus, the programmable read-only memories have 39 activated positions corresponding to the 39 switch settings on the potassium switch and 32 of such 8 bit outputs will be stored in register 133a with the remaining seven being stored in the register 133b to be addressed by the decoder 131. A suitable energizing supply 170 and resistors connect the output terminals of the decoder to the input terminals of the read-only memories to address the same. It will be noted that the one digit of the switch 130B will be directly connected to the memories 133a and 133b. Also one digit output terminal of the decoder 131 will be connected directly to memory 133a and through an inverter 175 for the memory 133b. This digit will provide the shift between the memories to locate the remaining seven outputs or those stored in memory 133b. The memories are similarly energized from a supply 170 and grounded as at 171. The output terminals of the same are connected in parallel and from a DC source 170 through resistors to one side of the input of a comparator 14. This comparator will compare the binary outputs of the read-only memories with the binary count from the line counters 155, as will be hereinafter identified.

Potassium switch 130 is also connected to the input of a digital encoder 131b which encoder has its output terminals energized from a source 170 through suitable resistors and to the input of a pair of read-only memories 134a and 134b. The encoder 131b like encoder 131a is DM74184 unit and is energized from the power supply 170 and grounded at 171. One digit from the second switch 130b is connected directly to the read-only memories. These units are similarly 6630-J manufactured by Monolithic Memories, Inc. They are programmable read-only memories in which the output from the binary decoder 131b is addressed to 32 memory positions in register 134a and seven in register 134b. The memories are programmed to provide a binary output which corresponds with the amount of sodium ions in solution A for the example given. For any setting of switch 30, there will be a corresponding amount of sodium ions present from the solution A delivered through the valve 15 from pump 40. The binary settings of this programmable read-only memory will correspond with the piston movement of piston 42 of pump 40 which will deliver the desired amount of potassium ions from the solution A. A suitable inverter 176 is connected to one of the input positions of the memory 134b and provide the shift to the seven storage positions in this memory. The output circuits thereof are energized from the DC power supply 170 through suitable resistors connecting the eight terminals of the memory respectively to the eight bit binary subtractor 143, shown in FIG. 6 as a pair of adders 143a and 143b connected in a subtract mode of operation. The adders 143a and 143b are four bit binary full adders taking the type number SN7483. They are energized respectively from the 5 volt DC source 170 and are grounded as at 171. Four bits of the binary outputs from the read-only memories 134a and 134b are connected respectively to the two adders, the other four bits of each adder coming from the sodium code memory 138 to be later described.

The sodium switch 135 is formed of two switch units 135a and 135b representing each digit of the switch selection from 25 to 45 for the example given for concentrate B. The concentrate solutions A and B contain a maximum of 125 and 145 mEq/l of sodium ions respectively and consequently, any combination of the two concentrates will have a range of sodium ions somewhere between 125 mEq/l and 145 mEq/l when diluted. Thus, the switch settings for the two switches 135a and 135b consider the last two digits of these numbers and the output of the switches in terms of binary coded decimals are sent through a series of adders in a subtract mode of operation to effect an outpu which is: X-25 in binary coded decimal where X is the switch selection. Thus, the switches 135a and 135b are connected respectively to adders 181, 182 and 183, and 184 in which the equation: $x - 25$ is solved in binary coded decimal. The adders are of the type designated SN7483 and the terminal locations listed on the drawing indicate the interconnection of the same. The 5 volt power supply 170 is connected to various of the input terminals set the value in the adders and interconnections and inverters 185a and 185b of the type N7404 are connected between the adders to complete the subtraction. The output of the adders in the subtract mode are fed as seven digits or bits to a binary coded decimal to a binary decoder 171 of the type N74184 which is energized from the power supply 170 and grounded as at 171. With the adders 181-184 connected in a conventional mode of subtract operation, the reference bits from the adders 182 and 183 are connected through an or gate 190 to provide the direct input to the programmable read-only memory 138. Memory 138 is a 256 bit bipolar programmable read-only memory of the type 6330-J. The numeral 25 in the subtract operation is provided through the connection of the power supply 170 to terminals 4, 5, 11 and 16 on adder 181 and terminals 5, 7, 13 and 16 on adder 182. The output of the decoder 171 or the four bits therefrom are energized from a power supply 170 through resistors with the outputs being directed to the read-only memory 138 to address the same. The output of the read-only memory is so programmed that it will provide 20 eight bit binary numbers corresponding to the binary output of the counter 155 for varying movement of the piston of cylinder 50 to provide the desired amount of mEq/l of sodium ions from the source B to correspond with the setting of the switches 135a and 135b. These eight bit outputs from the read-only memory 138 are connected to the adders 143a and 143b in the subtract mode of operation, the outputs being energized from the power supply 170 through resistors as shown. The eight bit output of the adders 143a and 143b in the subtract mode of operation is supplied to one input of the comparator 144. Comparator 144 is type DM8130, similar to the comparator 141. The opposite side of the comparator 144 receives an eight bit binary count from the counter 155, as will be hereinafter noted.

The line counter 155 is controlled by signals from the encoder block 120 which includes the photocell or photogransistor 122 and the light source or light emitting diode 122. As will be seen in FIG. 6, the 5 volt DC supply 170 is connected through a conductor 200, fixed and variable resistors 201, 202 to the light emitting diode 122, which is grounded as at 171. Photocell or phototransistor 122 receives energization through a resistor 205 and capacitor 206 in parallel to one side of the photo transistor, the other side of which is grounded. The resistor capacitor combination provides a level source of energization for the phototransistor to take a predetermined output therefrom when light from the diode strikes the phototransistor. This peaked output is AC coupled through a capacitor 210 to one input of an amplifier 215. The other input of the amplifier is energized through a resistor 214 connected to the ground terminal 171. Amplifier 215 is one chip of a quad amplifier identified as LM324 having a power circuit from a 12 volt DC source, as indicated at 220, with a ground at 222. The output is taken through a load resistor 225 which is connected to the ground conductor 171 and AC coupled through a capacitor 226 to the input of a monostable multivibrator or timer taking the type designation LM555. It is designed to generate a monostable pulse for each zero crossing cycle of the input signal. The terminal designation surrounding the same indicates the energization and control of the unit. The AC output is coupled to the trigger terminal which also receives energization through resistor 230 and diode 232 from the 5 volt DC source. The input supply and reset circuits are energized directly from the energizing source 170 with the threshold and discharge terminals being energized through a resistor 235 from source 170 and including a capacitor 236 to ground for pulse width determination. Similarly, the control voltage terminal is connected through a capacitor 237 to ground. A generally square wave output pulse from the output terminal is provided to the input of a pair of four bit counters 155a and 155b forming the counter 155. The counters are four bit binary counters taking the type number SN 7493. Two such counters are used with the final bit output of one being connected into the input of another. They are energized from the 5 volt reference source 170 and grounded at 171. A reset conductor 158 is connected to inputs of both counters to reset the same when a high voltage level is applied to the same and allowing count when a low voltage level is present. The output of the two counters provide an eight bit output which, as previously indicated, is fed to the comparators 141, 144 through the conductors indicated generally at 153 and 154.

The encoder or position sensor 120, as will be seen in the block diagram of FIG. 5, also provides a signal to the left and right end stop sensor block 160. In FIG. 6, it will be seen that the output of the phototransistor 122 is connected through a conductor 250 to one of the inputs of a pair of operational amplifiers indicated at 260 and 270 respectively, through resistors 261 and 262. The operational amplifiers are part of a quad amp 215 which will similarly be energized from the 12 volt source at 220 and grounded as at 222. The dual input amplifiers receive a voltage level signal from the 5 volt DC source 170 through resistors 264, 265, and 266 to ground with a tap between the resistors 264 and 265 leading to the second input of amplifier 260 and tap between the resistors 265 and 266 leading to the second input of amplifier 270. The voltages applied to the second inputs are adjusted through the resistors to different voltages for operation of the amplifier by the control signals. Thus, the left end sense amplifier will be provided with a very high output from the phototransistor 122 when the phototransistor is adjacent the darkened surface of the grid. At the right end of the grid which is transparent, the output of the phototransistor will be low. The reference levels of the two amplifiers are such that the outputs will normally be in a low conductive state with the amplifier output 260 going high when the left end of the grid is sensed. Similarly, the amplifier 270 will go to a high state when the right or clear end of the grid is sensed. As will be evident from the circuit, the inputs from the conductor 250 through the resistors 261 and 262 will be to opposite polarity terminals of the respective amplifiers to effect the turn on of the amplifiers under these conditions. The output of amplifier 260 is connected through a load resistor 271 to ground connection 171 and AC coupled through a capacitor 272 to the input terminal of a timer or a monostable multivibrator indicated at 280. The timer 280 is part of a dual timer unit identified as a dual timer LM556, the other half of which is shown at 285 as receiving the output from the amplifier 270 through a coupling capacitor 286. A suitable load resistor 287 connects the output of the amplifier to ground 171. Both timers are energized from the 5 volt DC source 170 through resistor and diode members indicated at 288 and 289 respectively. A pulse width circuit, formed of a resistor 291 and capacitor 292, is connected between the source 170 and ground and with a connection to the appropriate input terminals to the timers. In addition, suitable filtering capacitors 298 connected between the timers and ground for filtering purposes. The outputs of the respective timers 280, 285 are shown as conductors 300 and 301 respectively which conductors have impressed thereon a generally square pulsed output when the respective end portions of the grid are sensed by the phototransistor. These signals control or condition the logic of the respective drive circuits, as will be hereinafter noted.

The count signal from timer 234 along with the left and right end sense signals from timers 280 and 285 are connected into a delay and switching circuit whose output is impressed on conductor 158 for the purpose of starting and stopping the counters 155. Thus, it will be seen that the pulsed signals from the pulse shaping circuit 151 or timer 234 on conductor 240 is fed to the input of a four bit binary counter indicated at 305. The outputs from the timers 280 and 285 on conductors 300 and 301 respectively are connected to the input terminals of a nor gate 310 and a nand gate 315. The output of the nor gate is connected to the preset terminal of a flip-flop, indicated at 320, the output of which is taken at the terminal 14 through a conductor 321 to the reset terminals of the binary counter 305. The binary counter 305 as previously indicated is a four bit binary counter taking the type number N7493. Similarly, the flip-flop 320 is a master slave flip-flop with preset and clear taking the type number N7476. The nand gate 315 is one unit of a quadruple two input positive nand gate taking the type number N7400 and the nor gate 310 is a portion of a quadruple two input positive nor gate taking the type number N7402. The binary counter 305 is energized through its input terminal with energization being supplied from the 5 volt DC source indicated at 170. The output therefrom is coupled through a capacitor 326 at the 11 terminal thereof or its last bit to provide an input through a timer 330 which acts as a pulse shaper. Binary counter 305 has its output terminals connected together as indicated by the terminal designation of the drawing and the timer 330 is similar to the timer 234 taking the type number LM555. It has an input through a resistor 331 and diode 332 with certain terminals being directly connected to the DC source. A pulse width circuit formed by resistor 333 and capacitor 334 is connected between the source 170 and ground and it provides an input to the timer for time delay purposes. The output of the timer is taken at terminal 3 through a conductor 340 which is connected to the clock input of the slip-flop 350 whose output controls the counters 155. The circuit provided by the counter 305 and timer 320 provide a delay of eight counts to the start of operation of the counter 155 after the left end sense signal output is provided across conductor 300 to nor gate 310. The output of the nor gate is connected to the preset terminal of the master slave flip-flop 320 which changes sense as the left end signal is applied on the conductor 300 causing the nor gate 310 to go low. Thus, when the nor gate changes to a low output, the output of the flip-flop 320 at terminal 14 will be such as to permit the counter 305 to begin a count. This count will continue for eight counts until a positive pulse appears on the output of the counter which will energize the timer providing an output pulse at conductor 340 to provide a clock pulse to the flip-flop 350 switching the same to a low output. The pulse from the timer 330 also applies a signal to a nor gate 312 to clear flip-flop 320 resetting the same and changing the output therefrom. This stops the count of the binary counter 305. Thus, the output of the flip-flop 320 will go high to the input of the counter 305 preventing further count of the same. A suitable resistor 314 is connected between the conductor 340 and the input terminals of the nor gate with a capacitor 313 being connected from the resistor 314 to the ground terminal 171. This nor gate presets the flip-flop 320 after the timing function. It will not reset or switch again until the left end signal is applied thereto. The nand gate 315 similarly sets the flip-flop 350 to a high state providing a high signal on the conductor 158 to the counters 155 preventing operation of the same as the pistons move from right to left. This signal will be changed after the left end sense signal has been applied to the flip-flop 320 starting the counter 305 and after the delay of eight to ten counts. The output of the timer 330 provides a clock signal for changing the state of the output of the flip-flop 350 to permit operation of the counters 155. The particular delay of eight to ten counts after the left end stop is sensed provides for an equalization in pressure at valves 15, 25 and 35 as they shift from one fluid connection to another changing the flow of fluid from supplies to the cylinders to a condition where the fluid will flow from the cylinders into the output pipes.

The left and right end stop sense signals evidenced by the conductors 300 and 301 or the general cabling 161 in FIG. 5 is utilized to condition the operation of the valve drive units 19, 29 and 39 respectively.

The switching of valve 15 is effected from the comparator 141 which has an output at terminal 13 as indicated by the conductor 345. The comparator is energized from the 5 volt source and is grounded with the appropriate terminals at 171. The output conductor is fed to an or gate 355 whose output is connected to the clock terminal of a flip-flop 360 through a conductor 356. The or gate 355 is one half of a dual unit or gate having a dual input and identified as N7332 unit. The other half of the dual unit or gate 370 is fed from the output of the comparator 144 through a conductor 372 with the comparator 144 being energized from the source 170 and with suitable terminals grounded at 171. Flip-flop 360 is a master slave flip-flop with preset and clear taking the type number SN7476. The preset terminal of the flip-flop is controlled by a signal from the left stop end sense conductor 300 conducted through an inverter 347 through a conductor 352 to the preset terminals of a flip-flop 360 and another flip-flop 380 controlling the valve 25. The clear signal for flip-flop 360 is provided through the right end sense conductor 301 through an inverter 365 to one input of a nand gate 375 whose output is connected to the dual inputs of a nand gate 385 controlling the level of energization of the clear terminal of the flip-flop 360. The circuit also includes a failsafe feature in that for a zero potassium setting on the switch 130, the binary signals on the conductors addressing the code memories 133a and 133b, will be zero. Under these conditions, zero outputs are fed through a pair of triple input nor gates 391 and 392 with the outputs of the two nor gates being fed to a nand gate 395. The output of nand gate 395 is fed through a conductor 396 to the second input of the nand gate 375. Thus, whenever low signals are applied to the inputs of the nor gates 391 and 392, the high level outputs therefrom will provide high level input to the nand gate and low level output therefrom. This will assure that the nand gate 375 will not be in a condition to operate under such conditions regardless of the input signal from the right end sense conductor 300 through the inverter 365. The nand gates 395, 375, and 385 are all part of a quadruple, two input positive nand gate taking the type number SN7400. The energization circuit for this chip is shown at gate 385 wherein the input terminal is connected to the 5 volt DC supply 170 and the gate is grounded as at 171. Similarly, the nor gates 391 and 392 are part of a dual or gate having triple inputs and taking the type number SN7427. The inverter 365 is part of a six unit inverter taking the type number SN7407. In the operation of the flip-flops, 360, 380, the output signals are set to a high level in the master circuit when the left stop signal is received.

The output of the or gate 355 provides a clock pulse which changes the state of the outputs on flip-flops 360, 380. The signal output is reset by the clear signal obtained from the right end sense conductor 301 through the inverter 365 to insure that valves 15 and 25 are de-energized at the end of each stroke. The flip-flop 360 has its various energization circuits shown at the terminals marked thereon and is energized from the 5 volt supply 170 and grounded as at 171.

The output conductor 367 of flip-flop 360 is connected to one input of a nand gate 400 whose output switches the operation of a current amplifier, indicated at 410. The nand gate 400 has its second input received from a nand gate 415 whose input is obtained from a conductor 420. This conductor has a signal impressed thereon which will shut down the operation of valves 15 and 25 under conditions for cleaning the apparatus. The nand gate 415 provides such a conditioning circuit. This circuit is normally inoperative to prevent operation of the amplifier unless the signal is impressed on the conductor 420. Thus, the nand gate 415 will have a low level dual input thereon providing a high level output to the nand gate 400 and also to a nand gate 425. The latter receives its input from a conductor 426 or the output terminal of the flip-flop 380, to be hereinafter defined. The amplifier 410 is one unit of an LM3900 quad amplifier which is connected as a current amplifier. It is energized from the 5 volt DC source 170 and grounded as at 171 having a dual input. One input is through a resistor 430 connected to the 5 volt supply and the second input is through a resistor 431 connected to the output of nand gate 400. The presence of an output signal on gate 400 will raise the current output of the current amplifier to provide a voltage drop across the resistor 435 sufficient bias the base of a transistor 440 and turn transistor 440 on. The collector is connected from a 12 volt source 220 through a diode 441 with the emitter being grounded through a resistor 442. This provides an output which biases the base of a second transistor 450. The collector of this transistor is connected to the winding 460 of the control valve 15. The 12 volt supply 220 is connected to the opposite extremity of the winding or coil 460 to complete the energization circuit therefor with the emitter of this transistor 450 being grounded as at 171. Valve 25 is similarly controlled from the flip-flop 380 which receives its clock pulse from the or gate 370 which is part of a chip in which gate 355 is included. The output of the same is connected to the clock terminal of the flip-flop 380. The preset terminal is connected through the left end sense signal supplied through inverter 437 to conductor 352. The right end sense signal on conductor 301 is connected through inverter 470 to the clear input terminal of flip-flop 380. Inverter 470 is part of the chip of inverters which are energized from the 5 volt source 170 and are grounded as at 171. The output of the flip-flop 380, as indicated by the conductor 426, is connected through the nand gate 425 which also receives an input signal from the nand gate 415. The output of the nand gate 425 is connected through a resistor 472 to a current amplifier, indicated at 475, which is part of the quad amplifier indentified as LM 3900 of which amplifier 410 forms a part. The other input for the amplifier is connected from the 5 volt source 170 through a resistor 473. The output of amplifier 475 is connected through a bias resistor 480 to the base of a transistor 485 whose collector is connected through a diode 486 to the 12 volt supply 220. The emitter is grounded through a resistor 487. The emitter is coupled to a base of a second transistor 490 whose collector is energized through the diode 486 to a 12 volt supply with the collector being further connected through a coil or winding 495 of the valve 25 and to the 12 volt supply. The emitter is grounded as at 171. Thus, the current amplifiers provide a sufficient signal level from the flip-flop signals to bias the base of the transistors 440 and 485 to turn on the transistors 440 and 485 and hence operate the transistors 450 and 490 to control the energization to the coils 460 and 495 of the valves 15 and 25 respectively. It will be understood that the flip-flop 360, 380 will be conditioned for operation with the presense of a right end sense signal on the clear terminals of the respective flip-flops. As the left end signal is supplied to the flip-flops, the presence of the preset signal changes the state of the output thereof. The presence of a clock signal will change or alter the output signal to change the condition of operation of the resepctive current amplifiers and hence, energization of the valves. Under normal operation, the coils 460 and 495 will be de-energized and upon the presence of the left end sense signal, will change the condition of operation to energize the valves, permitting flow of fluid from the respective pump assemblies until such time as the comparators indicate piston travel to a point where sufficient volume has discharged from the cylinders to satisfy the requirements of the switch settings. At this point, the clock pulse will be received to change the condition of output of the amplifiers and de-energize the windings 460 or 495 changing the state of valve condition back to one in which the pump cylinders are connected to the sources of fluid.

The signals from the binary counter 155, as evidenced by the group of conductors 154, are fed not only to the comparator 146 but also the master cylinder calibrate module 156, shown generally in the drawings. The calibrate module is formed of a plurality of two input positive nand gates and a plurality of inverters each of which receive signals from the eight bit outputs of the binary counters 155. The nand gates are part of a quadruple two input positive nand gate taking the type number SN7408 and two such units are provided each being connected respectively to four of the bit outputs of the counters. As shown in the drawing, they are energized from the 5 volt DC supply 170 and grounded as at 171. Each of the bit output conductors 154 of the counters are also connected through the inverters taking the type number N7404. The outputs of the nand gate and the outputs of the inverters are connected respectively to contacts of eight switches, indicated generally at 510, which switches individually may be adjusted between one or the other of a pair of contacts to connect either the inverter or the nand gate to the respective bit conductor. Thus, the calibrate module 156 is formed of a plurality of and gates, indicated at 500, and to the plurality of inverters, indicated at 505, the inverters being similarly energized from the DC supply 170 and grounded as at 171. The outputs of the respective switches are tied to a common conductor 512 leading to the input of an eight input positive nand gate 515 which takes the type number N7430. The latter is energized from the 5 volt DC supply and grounded as at 171. The output of the nand gate 515 is connected through an inverter 520 and to the input of an or gate 525. The output of the or gate is connected through a conductor 526 to the clock input terminal of a flip-flop, indicated at 530. The flip-flop 530 is the type member SN7476 previously described. The clear pulse terminal of the flip flop 530 is connected to the right end sense signal conductor 301 through an inverter 535 similar to the flip-flops 360 and 380. The preset terminal of flip-flop 530 is connected from the left signal end stop conductor 300 through the inverter 347 and conductor 352. Flip-flop 530 has its output connected through a conductor 538 and a resistor 540 to one input of a current amplifier 550. The other input of a current amplifier is connected from a DC source 170 through a resistor 542. Current amplifier 550 is of the type LM3900 previously described, and its operation controls the energization of a transistor 560 through a bias resistor 561, to the base of the transistor. The transistor 560 is energized from the 12 volt supply 220 through a diode 562. The emitter is grounded through a resistor 563 which applies a signal to the base of a second transistor 570. The transistor 570 has its collector connected to the coil 580 of the valve 35 with the opposite end of the coil being connected to the 12 volt supply. The emitter of transistor 570 is grounded as at 171. Thus, this drive circuit 39 is similar to the drive circuits 19 and 29 for the valves 15 and 25. The output of the binary counter is directed through the calibrate module 156 which can be set through the inverters to respond to any desired binary count of the output of the binary counters 155. This will cause operation of the flip-flop 530 and control of the current amplifier 550 resulting in operation of the transistors 560 and 570 to control the energization of the coil 580 or to terminate the energization thereof. The positive nand gate responds to a condition where all eight inputs are the same. Thus, a logical one or high input voltage is required at the nand gate to provide the zero or low level output therefrom. This controls or establishes through the inverter 520 and nand gate 525, the clock pulse for controlling the energization of the current amplifier 550. The coil 580 becomes de-energized when the nand gates 515 changes state. This operation will control the length of the pumping stroke of the water cylinder 50. The flip-flop 530 is again conditioned by the presence of the right end sense signal and preset to energize the valve with the presence of the left end sense signal. The count of the counter 155 as the pistons move from left to right, pumping fluid from the respective cylinders, will control the operation of the respective comparators 141 and 144 to control the operation of the valves 15 and 25, and the calibrate module 156 will be adjusted through the switches 510 to terminate operation of the valve 35 in accord with the settings of the switches and the signals received at the respective and gates and inverters for the various bits of count.

While the circuit embodiment of FIGS. 5 and 6 makes use of conversion memories for converting from digital data to a pump position, it will be appreciated that there are a number of additional electronic techniques that can be used to achieve the same function.

In the operation of the system, reference should be made to FIGS. 1 and 5. Assume that the desired concentration values of sodium and potassium ions have been determined and entered on the switches 130, 135. The cylinders will fill with concentrate and water as the pistons move from the extreme right hand end of the cylinders as shown in FIG. 1 toward the left hand end. It will be appreciated that the left end of cylinders 41 and 51 are filled with the concentrate solutions drawn in by movement of the pistons toward the right hand end of the respective cylinders. The head vessels 16 and 26 will similarly be filled to a predetermined level as determined by level sensors associated therewith which operate the valves 13 and 23 respectively. When the head vessels are filled to a particular level, as determined by the level sensors, the valves 13 and 23 will be operated to a position which will force fluid from the left hand end of the cylinders back through the conduits 11 and 21 to the concentrate supply sources. If level of the fluid in the head vessels 16 and 26 is below a predetermined level, the level switches will permit operation of the valves 13 and 23 to switch to a point where fluid being ejected from the left hand end of the cylinders 41 and 51 will be directed to the head vessels 16 and 26 to bring the level to a desired point, after which the level switches will operate to force the remaining fluid, if any, back to the concentrate sources A and B. With the pistons in this starting position, the appropriate control will have operated the valves 15, 25 and 35 to a point where fluid will be drawn into the right hand end of the cylinders 41 and 51 from the head vessels 16 and 26 and the cylinder 61 will receive water from the tempered water supply through the pipe 33. As the pistons move simultaneously from right to left, the right hand cylinder ends fill. The drives 19, 29 and 39 will have been conditioned by the right end step sense portion of the position encoder 120 to adjust the respective drive so that the valves will not change operation during the direction of movement. When the left end stop sense is reached, the circuit 160 sends a signal through the conductors 161 to the respective drives causing each of the valves to switch to the opposite position with the three way valve connecting the right end port of the respective cylinders to the respective output pipes 48, 58 and 68. During right to left movement of the pistons, the line count signals transmitted to the line counter 155 will not be counted and the comparators 141 and 146 and calibrate module 156 will not receive any signals to operate the valve drive units 19, 29 and 39. When the left end stop sense signal is received by the drive circuits 19, 29 and 39 and the delay circuit, they will be conditioned to operate and the line count will begin after the delay. Movement of the pistons from left to right by the drive apparatus defines the pumping stroke for the proportioning pump during which the comparators will compare the signals from the respective conversion memories with the line counter for operation of the respective drive units. On this left to right stroke of the pump assemblies or the pumping stroke, dialysate concentrate from the sources 10 and 20 and water will be forced from the right hand end of the respective cylinders through the pipes 48, 58 and 68. The flow of concentrates will be directed through the pipes 36 to the left hand end of the pump 60 for mixing with any underflow being drawn through the pipe 76 and the standpipe 78 from the mixing vessel 70. As the movement of the pump pistons reaches the position corresponding to the required percentage of stroke for concentrate A, the digital comparator 141 causes the valve drive circuit 19 to switch the valve 15 from the valve position connecting the pipes 18 and 48 to one in which the remaining flow in the right hand end of the cylinder 41 will be directed back through the valve to the head vessel 16. Similarly, when the point is reached corresponding to the required stroke percentage for the concentrate B which may be before or after reaching the point of concentrate A, digital comparator 146 will cause drive circuit 29 to operate and move the valve 25 to a position where the remainder of the concentrate is directed back to the head vessel 26. The amounts of concentrates pumped through 48 and 58 are mixed in the left hand end of the cylinder 61 and will be ejected or moved to the vessel or holding chamber 70 on the next stroke of the piston 62 for pump 60 in the opposite direction, corresponding to the intake stroke for this cylinder. A suitable stirring device 71 within the vessel 70 aids in mixing. With this arrangement of parts, it will be noted that both sides of the pistons in each of the pump assemblies have liquid therein. Therefore, a positive prime condition exists in each of the pumping assemblies.

The vessel or chamber 70 will have sufficient volume to insure complete mixing of the concentrate solutions in water as an output is taken at the fluid conduit 90 to be delivered to a patient or usage area. An overflow pipe 77 is positioned in the chamber for overflow purposes.

As the apparatus reciprocates cyclically, dialysate drawn from the respective concentrate sources 10 and 20 together with the water is pumped to the mixing vessel and an area of usage. The overflow pipe is included in vessel 70 to prevent an overage when the pumping system is operating and the demand therefrom does not equal the output of the proportioning pump. The dialysate conductivity meters 12 and 22 are included in the lines from the sources 10 and 20 as appropriate warning circuitries against inadvertent interchanging of the solutions A and B. The concentration of concentrates A and B give conductivity meter readings which differ by approximately 20%. Appropriate warning device in the form of meter readings and/or warning signals from the conductivity meters enable the operator to insure that the apparatus provides the correct percentage of potassium and sodium ions in the dialysate solution as established by the input switches 130, 135.

The present invention thus provides means for precise proportioning for multiple fluid streams according to selectable proportionality ratios. It will be appreciated that different types of components, such as pump assemblies, valves and electronic circuits in the control means, can be used without departing from the scope of the invention. It will also be appreciated, as pointed out above, that while the preferred embodiment of the invention has been described with respect to dialysate proportioning, that the invention is equally applicable in other areas of the endeavor where multiple stream metering and proportioning is required.

What we claim is:

1. A blending system for preparation of variable hemodialysates from multiple fluid concentrate sources and water in controlled proportion, comprising: a plurality of cylinder and piston pump assemblies; means operating said pump assemblies simultaneously; fluid connection means for connecting said pump assemblies to a plurality of fluid sources to be metered, said fluid connection means including valve means for separately controlling fluid flow to and from each of said pump assemblies; position sensor means associated with said pump assemblies for producing signals indicative of the position of the pistons within the cylinders of said pump assemblies; control means connected to receive said position indicative signals and connected to said valve means in controlling relationship, said control means being operable to separately control the operation of the valve means associated with each of said pump assemblies as predetermined functions of piston position so as to control the volume of fluid metered by each of said pump assemblies during a pump stroke.

2. The system of claim 1 in which said plurality of cylinder and piston pump assemblies all have the same stroke dimension and in which at least one of said cylinders has a different diametrical dimension than the others of said pump assemblies.

3. The system of claim 2 wherein said means for operating the pumping assemblies for simultaneous operation moves said piston pump assemblies cyclically through intake and pumping strokes.

4. The system of claim 1 in which the valve means associated with each pump assembly includes valves having an intake passage and an outlet passage for selectively controlling flow of the fluids out of said cylinder in accord with the operation of said valve means.

5. The system of claim 4 in which the control means includes means for determining the amount of piston movement required for said volumes of fluids to be metered by each of said pump assemblies during a pump stroke.

6. The system of claim 4 in which the valve means associated with each pump assembly are operated so that said outlet passages of the valves are open while the intake passages are closed for metering said volume of fluid by each of the pump assemblies.

7. The system of claim 6 and including further fluid connection means connecting said outlet passage if certain of said valves to a mixing chamber and to one of said cylinder and piston assemblies at an extremity opposite to the connection of the fluid source thereto.

8. The system of claim 7 in which the control means includes a plurality of setting devices for establishing the amount of fluid from each source to be metered by the pump assemblies connected to said respective sources, means for converting the fluid amount settings to piston movement for each of the pistons of the pump assemblies, and with said control means including control circuits for comparing piston movement from said last named means with the piston positions to operate respectively the valve means associated with each of said pump assemblies.

9. The system of claim 1 in which the position sensor means includes means associated with and movable with said pump assemblies for producing signals in accord with movement of the pump assemblies.

10. The system of claim 1 in which said plurality of said fluid sources to be mixed include separate dialysate concentrates and a source of water and said fluid connection means connect respectively said sources through a separate one of said valve means to a separate one of said assemblies.

11. The system of claim 10 and including a mixing chamber connected to receive said metered volumes of fluids from said pump assemblies.

12. The system of claim 11 and including conductivity meters positioned in certain of said fluid connections and adapted to provide an indication of ion concentration of said source and departure of said ion concentration from a predetermined count.

13. A blending system for preparation of variable hemodialysates from a plurality of fluid concentrate sources and water in controlled proportion comprising, a plurality of sources of fluid to be mixed in a predetermined proportion; pump assemblies for each source of fluid, said pump assemblies having a double ended cylinder and piston slidable therein for moving fluid respectively from each of said sources, fluid connection means connecting one end of each cylinder to said respective source through a valve means; certain of said cylinders having fluid connection means connecting said source of fluid to the other end of said cylinders; said valve means for each of said cylinders having a passage therethrough for permitting flow of said fluid from said respective sources to said one end of said cylinder with the same direction of piston movement and a second passage for permitting flow of said fluid from said one end of said cylinders with an opposite direction of piston movement; a holding and mixing tank; additional fluid connection means connecting the second passage of each of said valves for said cylinders to said holding and mixing tank and to said other end of another of said cylinders; means linking all of said pistons together for simultaneous movement in the same direction; and means for operating said valve means including setting devices and means responsive to movement of said respective pistons to meter the predetermined proportions of said fluid from each of said sources.

14. The system of claim 13 in which the valve means for said certain of said cylinders are operated to close said second passages corresponding with predetermined piston movement to meter said predetermined amounts of said fluid from said sources.

15. The system of claim 14 in which each of said cylinders have fluid in each end thereof and on either side of said piston for all directions of the piston movement.

16. The system of claim 15 in which said other end of said another of said cylinders is a mixing chamber to receive fluid from said one end of each of said cylinders.

17. The system of claim 16 in which said setting devices include means for establishing desired amounts of piston movement in said certain of said cylinders to move fluid through said second passages.

18. The system of claim 17 in which the means for operating said valve includes a piston position sensor associated with the pump assemblies for producing signals indicative of the position of the pistons within the respective cylinders of said pump assemblies, and control means connected to receive said position indicative signals and connected to said valve means to separately control the operation of the valve means associated with each of said pump assemblies as predetermined functions of piston position so as to control the fluid metered by each of said pump assemblies to said predetermined proportions during a pumping stroke.

19. The system of claim 18 in which the pump assemblies are mounted in a single mounting frame and the shafts for the pistons are connected to a plate reciprocated relative to the frame.

20. The system of claim 19 in which the position sensor is an optical sensor including a light source and photo cell mounted on a shaft and connected to said plate being movable relative to a grid having a plurality of parallel lines formed of alternately opaque and transparent media mounted in said mounting frame.

21. The system of claim 20 and including a drive means connected to said plate for reciprocating said pistons in said cylinders.

22. The system of claim 21 in which the other of said cylinders has a heater means included in said fluid connection from said source to said valve means.

23. The system of claim 22 in which said certain of said cylinders have conductivity meters included in said fluid connections from said source to said valve means.

24. The system of claim 22 in which the fluids of sources connected to said certain of said cylinders include sodium and concentrate solutions having ions sodium and potassium respectively and in which the source for the other of said cylinders is water with the mixed fluids being a dialysate solution.

* * * * *